United States Patent [19]

Persson

[11] Patent Number: 5,405,361

[45] Date of Patent: Apr. 11, 1995

[54] EXTERNAL DEFIBRILLATOR CIRCUIT

[75] Inventor: Eric Persson, Minnetonka, Minn.

[73] Assignee: SurViva Link Corporation, Minneapolis, Minn.

[21] Appl. No.: 31,532

[22] Filed: Mar. 15, 1993

[51] Int. Cl.$^6$ ............................................. A61N 1/39
[52] U.S. Cl. ................................................. 607/5
[58] Field of Search ......................... 607/4, 5, 7, 10, 12

[56] References Cited

U.S. PATENT DOCUMENTS

| 3,706,313 | 12/1972 | Milani et al. | |
|---|---|---|---|
| 3,886,950 | 6/1975 | Ukkestad | |
| 4,050,004 | 9/1977 | Greatbach | 607/12 X |
| 4,566,457 | 1/1986 | Stemple | 607/5 X |
| 4,823,796 | 5/1989 | Benson | |

FOREIGN PATENT DOCUMENTS

| 2589462 | 7/1964 | Australia | |
|---|---|---|---|
| 0445800 | 9/1991 | European Pat. Off. | 607/5 |
| 0487776 | 6/1992 | European Pat. Off. | 607/5 |

Primary Examiner—Lee S. Cohen
Assistant Examiner—Jeffrey R. Jastrzab
Attorney, Agent, or Firm—Joel Skinner

[57] ABSTRACT

A portable, automatic external defibrillator, comprising a plurality of capacitors; a capacitor charging circuit; connections from the capacitors to a patient body; and a plurality of semiconductor switches arranged to connect the capacitors to the charging circuit and to the patient body.

1 Claim, 4 Drawing Sheets

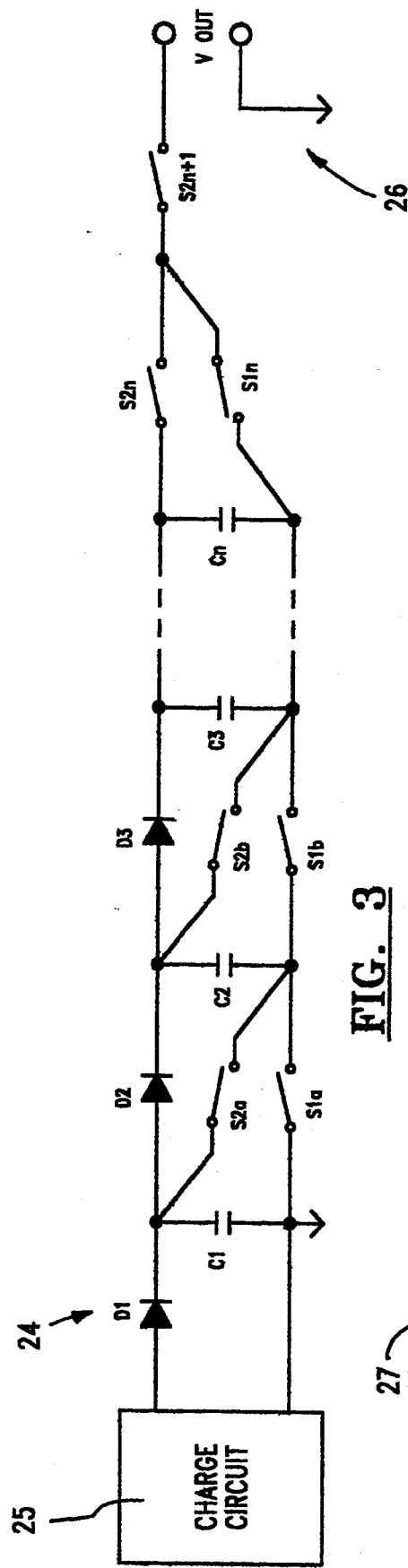

5,405,361

EXTERNAL DEFIBRILLATOR CIRCUIT

BACKGROUND OF THE INVENTION

This invention relates to medical therapeutic apparatus. More particularly, this invention relates to electronic circuitry for use in an external defibrillator apparatus. The apparatus of this invention provides an improved, low cost, portable external defibrillator.

The external defibrillator is a well recognized and important tool for resuscitating cardiac arrest patients. Defibrillation of the human heart is accomplished by applying an electrical waveform to the cardiac muscle with appropriate electrodes, causing the cessation of rapid uncoordinated contractions of the heart (fibrillation) and restoration of normal beating of the heart.

In the past, external defibrillators have been limited in use to hospitals, ambulances and other specialized locations. However, the health care community has recently called for more widespread disposition and use of automatic external defibrillators, particularly those which are portable. For example, it has been recognized that the placement of portable external defibrillators in nursing homes, sports facilities, and various other public and private facilities could save many lives in the setting of a cardiac arrest. Another proposal for the widespread placement of portable external defibrillators is with public safety officials such as police squad cars and the like.

A primary factor in limiting the dissemination of portable external defibrillators is their cost. A typical portable external defibrillator costs approximately $5000 to 10,000. Costs for portable external defibrillators are high mainly due to the high costs of circuit components which are able to deal with extremely high voltages and currents utilized in cardiac defibrillation.

Despite the need in the art for a portable external defibrillator apparatus and circuitry therefor which overcomes the limitations and problems of the prior art, none insofar as is known has been proposed or developed. Accordingly, it is an object of the present invention to provide a portable automatic external defibrillator apparatus which overcomes the limitations and shortcomings of the prior art. Particularly, it is an object of this invention to provide an improved portable external defibrillator apparatus which is reliable, durable, and effective at delivering defibrillating charges to the body of a patient. Another object of this invention is to provide defibrillation circuitry which is inexpensive to construct so that portable external defibrillators may be disseminated in a variety of settings and locations and for use by a variety of skilled and semiskilled medical personnel. A specific object of this invention is to provide circuitry for charging a plurality of capacitors in parallel and for discharging them in series which utilizes a plurality of semiconductor switches.

SUMMARY OF THE INVENTION

The present invention provides an external defibrillator apparatus, comprising:
a) a plurality of capacitors;
b) means to charge the capacitors;
c) means to connect the capacitors to a patient; and
b) means to switch the capacitors between the charge means and the connection means to thereby charge and discharge the capacitors, the switch means including a plurality of semiconductor switch elements.

In a preferred embodiment, the invention provides a low cost, portable automatic external defibrillator apparatus, comprising:
a) "x" number of capacitors, where "x" is greater than 1, selectively connected in parallel with each other, each capacitor having first and second electrodes;
b) means to charge the capacitors;
c) at least two medical connection electrodes, communicatively connectible to the capacitors and for placement on the body of a patient;
d) "x−1" number of the first semiconductor switches disposed in series with each other, each between the first electrode of capacitor "n" and the first electrode of capacitor "n+1" and "n" number of second semiconductor switches disposed in series with each other, each between the second electrode of capacitor "n" and the first electrode of capacitor "n+1"; and
e) "x" number of diodes disposed in series with each other, each being disposed between the second electrode of capacitor "n" and the second electrode of capacitor "n+1", whereby the capacitors charge in parallel and discharge in series.

These and other benefits of this invention will become clear from the following description by reference to the drawings.

BRIEF DESCRIPTION OF THE DRAWINGS

FIG. 3 is a simplified schematic diagram of one embodiment of the defibrillator circuit of the present invention.

FIG. 4 is a schematic diagram of a portion of an alternative embodiment of the defibrillator circuit of this invention.

DESCRIPTION OF THE PREFERRED EMBODIMENT

Figure 1:
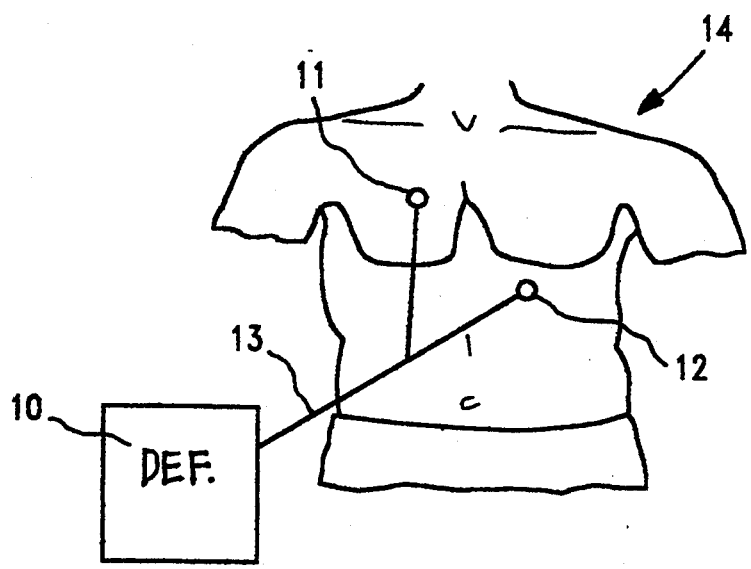
FIG. 1 is a simplified diagram showing the operative connection of a typical portable external defibrillator to the chest region of a patient.
Figure 2:
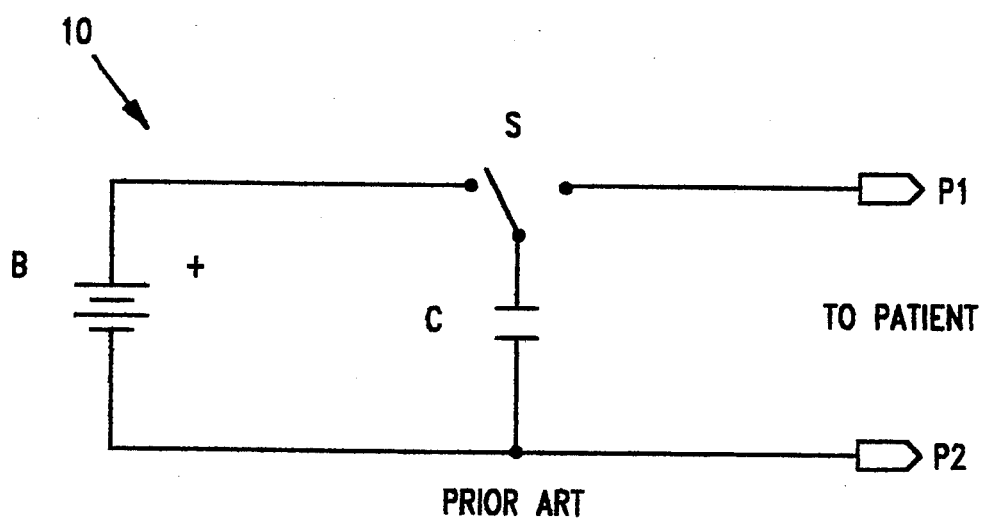
FIG. 2 is a simplified schematic diagram of a prior art defibrillator circuit.

Referring to FIGS. 1 and 2, the external defibrillator 10 is electrically linked to at least two electrodes 11 and 12 via a cable set 13. The electrodes 11 and 12 are shown operatively disposed on the chest region of a patient 14. FIG. 2 shows a simplified version of the internal circuitry of a prior art external defibrillator 10. Basically, the circuit comprises a battery based power source B connected to a capacitor or other charge storage element or circuit C and a switch S which enables connection of the battery B to the capacitor C during a charge accumulation state, and connection of the capacitor C to the electrodes 11 and 12 during a discharge state where the stored charge is being delivered to the patient body 14 for cardiac defibrillation purposes.

In prior art defibrillators, the capacitor and switch are the two components of the device which contribute most significantly to the overall cost of manufacture. The defibrillator must be able to discharge a large amount of energy, on the order of 400 Joules, in order to reliably defibrillate the patient. Prior art defibrillators have met this requirement by utilizing a single, rather large capacitor. The cost of such a component is significant. Also due to the relatively high voltages and currents involved, the potential for leakage voltages, and because of reliability constraints, prior art defibrillators typically utilize mechanical relay devices for switching. These components are also costly. As was previously discussed, cost factors have heretofore made it very difficult to disseminate portable external defibrillators on a widespread basis.

Referring to FIG. 3, a basic embodiment of circuitry 24, of the present invention, for a portable external defibrillator is shown comprising a plurality of semiconductor switch elements S in conjunction with a charging circuit 25 and capacitors C. Semiconductor devices such as silicon-controlled rectifiers (SCR's) are commonly available at a relatively low cost. A plurality of 400 to 1200 V thyristors may be utilized for example to control switching from charge and discharge states in the defibrillator. These components are mass produced for devices such as light dimmer switches and may thus be obtained inexpensively.

The circuit 24 comprises a plurality of capacitors $C(1-n)$, preferably six, connected to a charging circuit 25 and selectively in parallel with respect to each other. The capacitor charging circuit 25 is a current limited voltage source. Small, approximately 400 V capacitors are also mass produced for energy storage in camera flash systems and the like, and are thus inexpensive to obtain. The configuration of the capacitors C in parallel eliminates the voltage imbalance problem inherent in charging electrolytic capacitors in series. For convenience of reference, the electrodes or terminals of capacitors $C(1-n)$ are designated "second" (positive) at the top end of the circuit 24, and "first" (negative) at the bottom end of the circuit 24.

Still referring to FIG. 3, the circuit 24 is constructed and arranged to allow for the charging of the capacitors $C(1-n)$ in parallel and for discharge in series to deliver required high voltage defibrillating shocks. This is accomplished via the utilization of first semiconductor switches $S1(a-n)$ and second $S2(a-n)$, primarily.

Five switches $S1(a-n)$ are disposed in series with respect to each other, each individual switch $S1n$ being disposed between the first electrode of each individual capacitor $Cn$ and the first electrode of its adjacent capacitor $Cn+1$. The first electrode of capacitor $C1$ is shown to be connected to ground. Six switches $S2(a-n)$ are disposed essentially in series with each other, each individual switch $S2n$ being disposed between the second electrode of each individual capacitor $Cn$ and the first electrode of its adjacent capacitor $Cn+1$. When switches $S1(a-n)$ are turned on the capacitors C are connected in parallel.

The last switch $S2n$ in the series is shown to be connected between the first electrode of the last capacitor $Cn$ in the circuit 24 and the output section 26 of the circuit 24. When switches $S2(a-n)$ are turned on the capacitors C are now effectively in series, with the sum of their voltage appearing at Vout.

A plurality of diodes $D(1-n)$ are connected in series with each other, the anodes of which are disposed towards the capacitor charging circuit 25. Diode D1 is disposed between the charging circuit 25 and the second electrode of capacitor C1. The remaining diodes D2-Dn are disposed between the second electrode of each capacitor $Cn$ and the second electrode of its adjacent capacitor $Cn+1$. These diodes allow for parallel charging of the capacitors C, and become reversed biased when switches $S2(a-n)$ are turned on.

In a charge-up state, switches $S2(a-n)$ are open and switches $S1(a-n)$ are closed. The capacitors $C1-n$ charge in parallel. Switches S1 can be implemented by an optocoupled transistor, such as that shown in FIG. 5A as OP1, for example. No component of this circuit 24 will see a voltage higher than the voltage present on one capacitor C. As a result, where this circuit 24 has six capacitors C and a peak circuit 24 output of approximately 2000 V, no capacitor C will see more than approximately 333 volts. This allows the use of relatively inexpensive components having the same breakdown voltage of approximately 400 V. Each capacitor $Cn+1$ has one (1) diode drop less voltage than its adjacent capacitor $Cn$. An additional benefit of this low voltage circuit configuration is that leakage currents, which are inherent in semiconductor components and on the circuit boards, for example, at high voltages, are minimized.

During discharge to a patient, switches $S2(a-n)$ are closed and switches $S1(a-n)$ are open. The capacitors $C1-n$ thus discharge in series, delivering current to the patient's heart. Switches S2 can be implemented via a variety of semiconductor means, but a thyristor, triac or transistor are preferred for cost reasons. Triggering of these switches $S2(a-n)$ is accomplished via a galvanically isolated circuit. Triggering is preferably accomplished magnetically via gate drive transformers to simultaneously trigger switches S2. An optically coupled SCR or triac may alternatively be used.

Referring to FIG. 4, a segment 27 of a preferred circuit embodiment is shown. Current limit and rise time limit in the switches S2 is implemented by placing a resistor R1 and an inductor L1 in series with each capacitor $Cn$. Additionally, a parallel dump switch S3 is shown added across the network C1/L1/R1 to deliver an appropriate defibrillation waveform with a rapid drop in voltage at a predetermined time. This is particularly important when thyristors, which are difficult to turn off, are utilized in switching. A clamp diode $D2(a-n)$ is added across each capacitor $Cn$ to prevent that capacitor $Cn$ from becoming reverse biased. In addition, a flyback diode $D3(a-n)$ may be included across each inductor $Ln$ if a power transistor, which can be turned off as well as on, is used in the circuit.

Figure 5A:
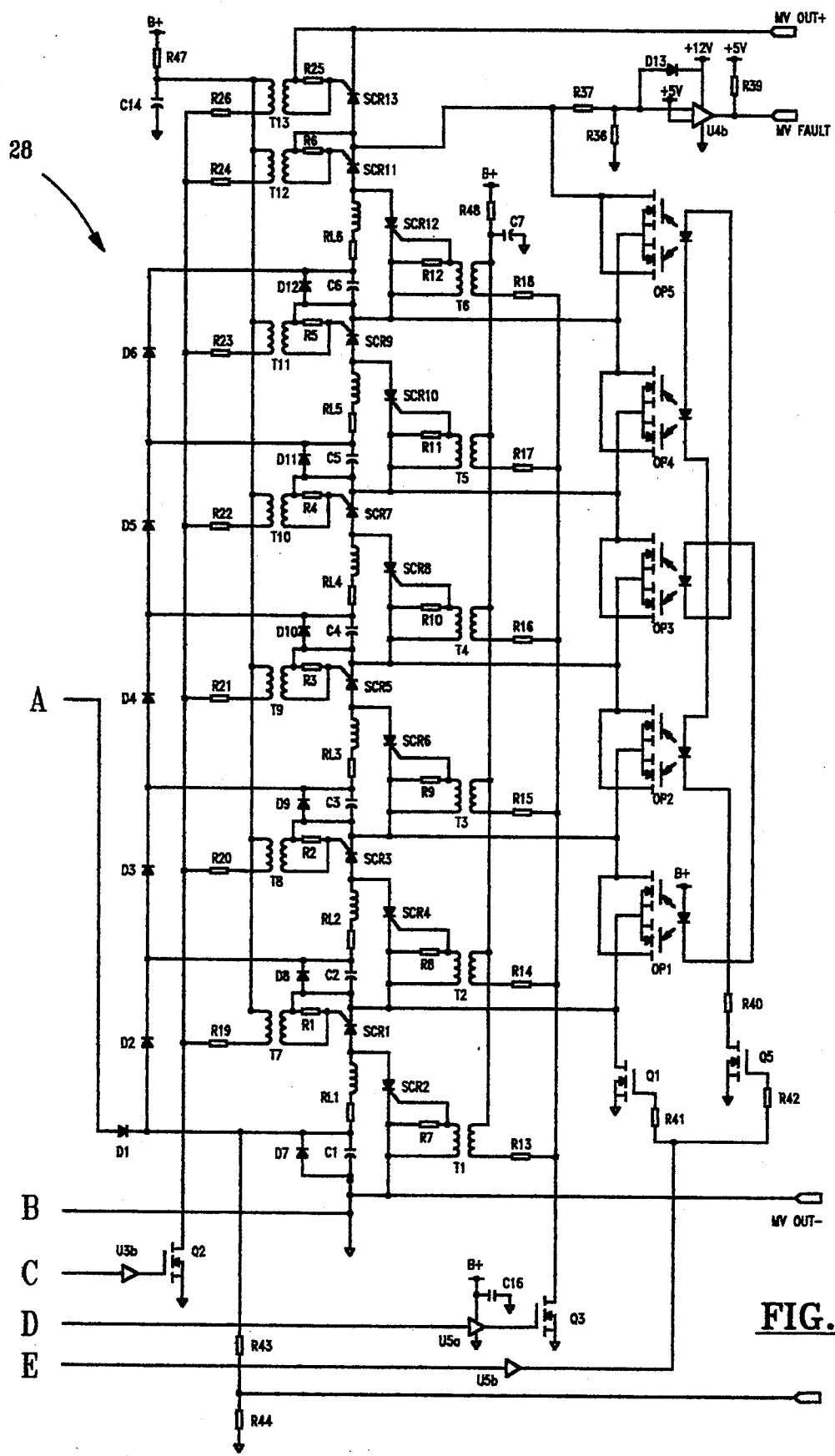
FIGS. 5A & 5B are schematic diagrams of the most preferred embodiment of the defibrillator circuit of this invention.
Figure 5B:
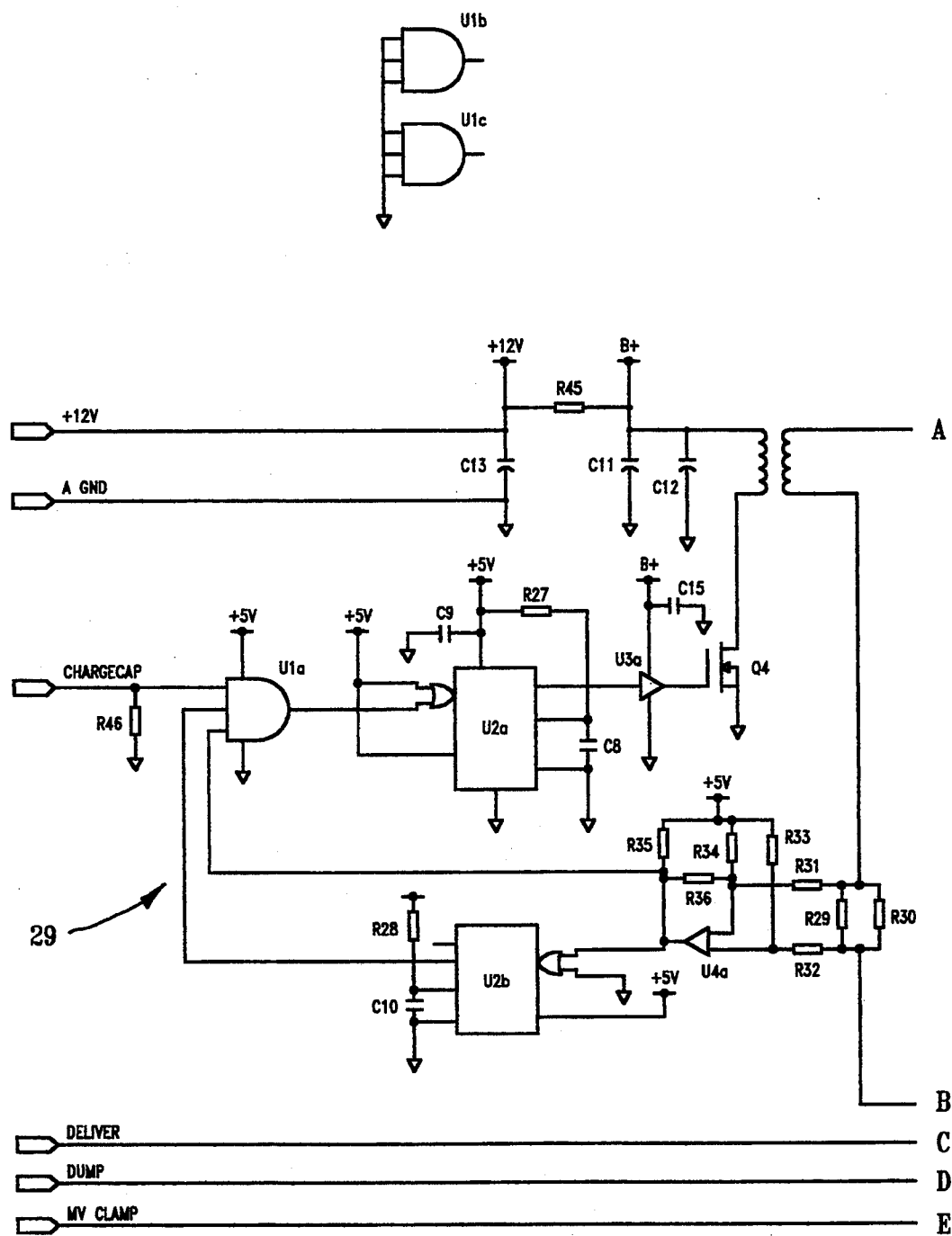

Referring to FIGS. 5A & 5B, the most preferred circuit embodiment 28 of this invention basically comprises a voltage converter circuit 29, six capacitors $C1-6$ connected in parallel with one another with respect to HV OUT "+" and "−". Seven diodes D1-7 are connected in series, each between first electrodes of the capacitors C1-6. First semiconductor switches Q1,OP1,2,3, and 4 are connected in series, each between second electrodes of adjacent capacitors C1-6. The first semiconductor switches OP1,2,3, and 4 are shown to be optocoupled transistors, and Q1 is a conventional FET. Op5 is an additional switch which is used to shunt any leakage currents. Second semiconductor switches SCR1,3,5,7,9 and 11 are connected between the first and second electrodes of adjacent capacitors C. Second switches SCR 1,3,5,7,9 and 11 are shown to be magnetically triggered SCR's. As was previously discussed, the essential characteristic in the behavior of this circuit 28 is that the capacitors C1-6 charge in parallel via closure of first switches Q1,OP1,2,3, and 4, and discharge in series via closure of second switches SCR1,3,5,7,9 and 11.

Capacitor C1 preferably has a resistor R1 and an inductor L1 (combination RL1) disposed in series with it. The remaining capacitors C2–6 are similarly configured with RL networks to limit peak current and rise time in switches SCR1,3,5,7,9 and 11 during an output, or switches SCR2,4,6,8,10 and 12 during a dump. Clamp diodes D7,8,9,10,11 and 12 are also shown disposed with respect to these capacitors. Finally, switches SCR2,4,6,8,10,and 12 are shown disposed in parallel across capacitor networks C1–6, respectively, to dump charge at a predetermined time in the discharge cycle. Preferably, switches SCR2,4,6,8,10 and 12 are magnetically triggered SCR's.

SCR 13 is shown disposed at the final node anterior to HV Out(+) to prevent leakage of DC current upon capacitor charge up. SCR 13 is triggered simultaneously with SCR1,3,5,7,9 and 11 and serves as a redundant switch to minimize leakage currents to the patient when capacitors are charged.

As many changes are possible to the embodiments of this invention utilizing the teachings thereof, the descriptions above, and the accompanying drawings should be interpreted in the illustrative and not the limited sense.

That which is claimed is:

1. A low cost, portable, automatic external defibrillator apparatus, comprising:
   a) "x" number of capacitors, where "x" is greater than 1, selectively connected in parallel with each other, each capacitors having first and second electrodes;
   b) means for charging said capacitors;
   c) at least two medical connection electrodes, communicatively connected to said capacitors via conductive leads, and for placement on the body of a patient;
   d) a charge path formed by said capacitors and further comprising "x−1" number of first semiconductor switches disposed in series with each other, each between said first electrode of a capacitor "n" and said first electrode of a capacitor "n+1", said charge path charging said capacitors in parallel;
   e) an independent discharge path formed by said capacitors and further comprising;
      (i) "x" number of second semiconductor switches disposed in series with each other, each between said second electrode of capacitor "n" and said first electrode of capacitor "n+1", said discharge path discharging said capacitors in series, simultaneously; and
      (ii) a low resistance current limiter disposed in series with each said capacitor, said current limiters being the only elements connected in series between said capacitors and their respective said second semiconductor switches, each said current limiter consisting of a resistor and an inductor, whereby said discharge path has a resistance of less than 10 ohms;
   f) a charge dump path formed by said capacitors and further comprising a plurality of third semiconductor switches, each being disposed across a respective said capacitor for dumping charge from said capacitors at a predetermined time; and
   g) "x" number of diodes disposed in series with each other, each being disposed between said second electrode of said capacitor "n" and said second electrode of said capacitor "n+1", whereby the apparatus delivers a sharply truncated waveform upon discharge to the patient.

* * * * *